United States Patent [19]

Finfinger et al.

[11] Patent Number: 4,679,435
[45] Date of Patent: Jul. 14, 1987

[54] GAS CONTENT DETERMINATION OF EVAPORITE FORMATIONS USING ACOUSTIC EMISSIONS DURING DISSOLUTION

[75] Inventors: Gerald L. Finfinger, West Mifflin; Roger L. King; Thomas E. Marshall, both of Pittsburgh, all of Pa.

[73] Assignee: The United States of America as represented by the Secretary of the Interior, Washington, D.C.

[21] Appl. No.: 838,490

[22] Filed: Mar. 11, 1986

[51] Int. Cl.$^4$ .............................................. G01N 29/00
[52] U.S. Cl. ......................................... 73/594; 73/19; 73/587
[58] Field of Search ................... 73/19, 153, 587, 590, 73/594

[56] References Cited

U.S. PATENT DOCUMENTS 2,573,390 10/1951 Blanchard ............................. 73/590
2,756,585 7/1956 Irby ....................................... 73/19
4,208,914 6/1980 Feist ...................................... 73/590

FOREIGN PATENT DOCUMENTS 829571 3/1960 United Kingdom ................... 73/590

Primary Examiner—John Chapman
Attorney, Agent, or Firm—Thomas Zack; E. Philip Koltos

[57] ABSTRACT

The present invention provides a method which avoids the expense and danger of previous methods used to discover gas contained in geological formations to be mined. Specifically, it has been found that increasing gas contents of evaporite samples emit increasing levels of sound when dissolved in water. By recording the sounds given off by small grab samples taken from within the mine and from the specific formation to be mined, the volume of gas in the sample can be ascertained and gas liberation during mining operations may be predicted. The method comprises the steps of: obtaining a sample; placing it into water and placing the water and sample into a sound-proof chamber; recording the acoustic emissions given off as the sample dissolves; using the recorded acoustic emissions to determine the presence and volume of gas in the sample; and predicting the volume of gas in the evaporite formation to be mined.

5 Claims, 3 Drawing Figures

GAS CONTENT DETERMINATION OF EVAPORITE FORMATIONS USING ACOUSTIC EMISSIONS DURING DISSOLUTION

TECHNICAL FIELD

The present invention relates in general to methods for assessing potential gas emissions from geological formations into a mine environment. More particularly, the invention relates to a process including the appraisal of acoustic emissions which determines, without extensive exploratory drilling and laboratory analysis, the presence and volume of gas in an evaporite formation sample.

BACKGROUND OF THE INVENTION—PRIOR ART

In the mining or mineral extraction industry, it is well known that as a result of mining operations, various gases contained within the geological formations in which the mining is being done may be released into the mine environment. Depending on the amount or volume of gas released may vary from virtually none to upwards of hundreds of thousands of cubic feet and consequently, ventilation requirements and costs have correspondingly varied. Further, the ventilation requirements were unpredictable until after extensive exploratory drilling was carried out. Prior to the present invention there was no simple method for conveniently, accurately and quickly assessing the amount of gas which may be released by mining operations other than undertaking expensive exploratory drilling and laboratory analysis of samples obtained in advance of actual mining. An example of such laboratory analysis is found in U.S. Pat. No. 2,749,220 (to Rochon) which discloses a method for measuring the gas content of earth samples. The process involves vacuum extraction of the gas from the sample, and subsequent "hot filament" testing, as well as a complicated system of chambers, conduits and valves. Rochon does not disclose the concept of measuring acoustic emissions.

Relative to the novel use of acoustic emissions in the process of the present invention, in "General Principles of Acoustic Emission", *Material Evaluation*, Oct. 1981, vol. 39, pp 1000–1002, Lenair discloses that the principle of acoustic emission testing or analyzing of various physical phenomena is well known. Possible uses suggested include assessing the behavior of materials and specifically, "rock mechanics", as well as possible applications in the petrochemical industry. However, there is no suggestion that acoustic emission analysis may be used to assess gas presence and volume in geological formations.

There are other patents which disclose the use of acoustic emission or behavior. For example, Kanagama et al suggests monitoring acoustic emissions produced by continuously increasing the loading of a rock sample, but rather than to assess gas content, the process is used to determine the hysteretic maximum stress. U.S. Pat. No. 3,865,201 assesses acoustic emission, but to determine formation pressures in the vicinity of a drill bit. None of these references address the long existent need in the mining industry for a reliable, quick, accurate and simple method to determine gas content in an evaporite formation so that a safe mine environment may be maintained.

DISCLOSURE OF THE INVENTION

Therefore, in response to the need in the industry, it is a major, important object of the present invention to ensure and promote a safe mineral extraction environment.

It is a specific object of the present invention to provide a method which can be used to evaluate the potentially hazardous emission of gas into a mine environment.

It is a further specific object of the present invention to provide a method which can be used to determine the amount of gas contained within an evaporite formation, prior to mining, by measuring the acoustic emission levels during dissolution of evaporite samples.

It is another object to provide a method of determining the gas contained in an evaporite formation that is both accurate and rapid, and may be performed in non-laboratory circumstances.

These and other objects are achieved by providing a method to assess potential gas emissions comprising the steps of:

(a) obtaining a small grab sample from within the mine complex and from the formation to be mined;

(b) placing the sample in a container of water which is then placed within a sound-proof chamber;

(c) recording the acoustic emissions from said sample as it dissolves in said water; and (d) examining the recorded sound levels and interpreting said levels to determine the amount of gas within the area to be mined.

BEST MODE FOR CARRYING OUT THE INVENTION

In order to determine the potential for release of hazardous gases into the mine environment during the extraction of minerals, it is customary to carry out exploratory drilling in advance of mining. Samples obtained thereby are sent to laboratories for traditional, expensive testing, such as gas chromatography analysis. However, because such exploratory drilling is extremely expensive, in many cases it may not be done and potentially hazardous gas conditions are not identified until mine entries encounter the dangerous gas enriched zones.

The process of the present invention is carried out by first procuring a small grab sample from within the mine complex and from the specific evaporite formation to be mined. The sample is inserted into a beaker or other container of water and the container placed into a sound-proof chamber. The sound-proof chamber is necessary to prevent interference from external noise sources and may be constructed of conventional, well-known materials capable of excluding or damping enough noise to ensure accurate acoustic emission perception and recordation.

A microphone is located within the chamber, in a relationship such that any acoustic emissions produced as the evaporite sample dissolves in the water may be accurately sensed. The microphone is connected to a strip-chart recorder that may be running at a speed of five centimeters per minute. Acoustic emissions produced by the dissolution of the sample may be recorded for a time period deemed long enough to ensure accuracy and for comparative purposes. For example, a recording period of approximately five minutes may be appropriate.

Following the completion of the test or tests, the recorded acoustic emission levels are examined and the amount of gas contained by the sample can be determined. From the assessed volume of gas in the sample, gas liberation during mining operations may be predicted and required ventilation or evacuation procedures may be implemented prior to actual mining operations and before hazardous gas produces dangerous conditions.

The results of the process of the present invention are shown by the following examples.

EXAMPLE 1

Figure 1:
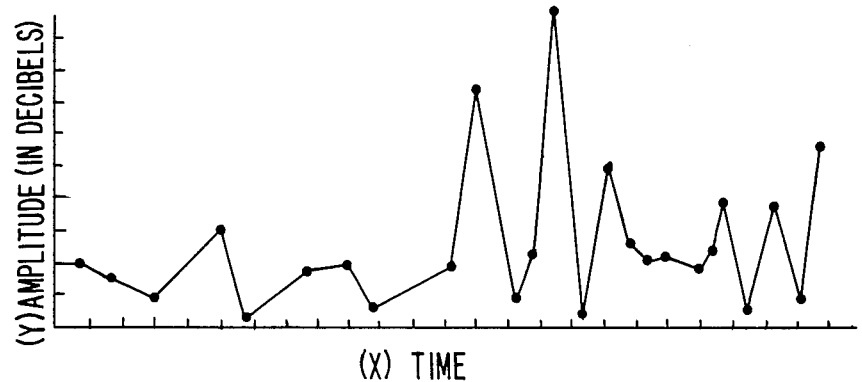
FIG. 1 is a graphic representation expressed in decibels per unit of time of the level of acoustic emissions from the dissolution in water of an evaporite formation sample containing essentially no gas.

A small grab sample was procured from an evaporite formation containing essentially no gas. The sample was placed into a beaker of water and the beaker, containing the water and sample immersed therein, was placed into a sound-proof chamber. A microphone positioned in the chamber sensed and permitted the recording by an acoustic recording device of the level of acoustic emissions produced as the sample underwent dissolution. FIG. 1 is a graphic representation of the results of the decibel level of the recorded acousteic emissions produced by the sample in a specific period of time (5 minutes).

EXAMPLE 2

Figure 2:
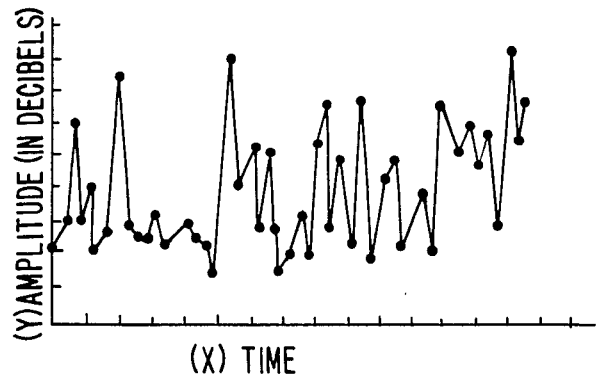
FIG. 2 is a graphic representation expressed in decibels per unit of time of the level of acoustic emissions from the dissolution in water of an evaporite formation sample containing 4 $cm^3/100$ gm of gas.

A sample was procured from an evaporite formation containing 4 $cm^3/100$ gm of gas. The sample was placed into a beaker of water and the beaker, containing the water and sample immersed therein, was placed into the sound-proof chamber. The level of acoustic emissions produced as the sample underwent dissolution in the water for the same time period as in Example 1 was recorded. FIG. 2 is a graphic representation of the decibel level over time of the acoustic emissions produced by the sample.

EXAMPLE 3

Figure 3:
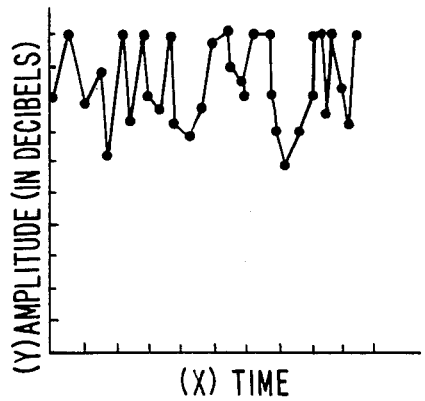
FIG. 3 is a graphic representation expressed in decibels per unit of time of the level of acoustic emissions from the dissolution in water of an evaporite formation sample containing 8 $cm^3/100$ gm of gas.

In this example, the same process as that followed in Example 1 and 2 was repeated, but the sample was taken from an evaporite formation containing 8 $cm^3/100$ gm of gas. The recorded level of acoustic emissions are graphically depicted in FIG. 3.

From the foregoing examples, it can be seen that the gas content of evaporite formation may be indicated by the process of the present invention. As the strip-recorded acoustic emissions approach levels indicated by FIG. 3, the operators will know that the potential exists for large gas emissions during mining operations and will be able to undertake appropriate ventilation measures prior to mine entry.

The advantages of the present novel process are: the procedure does not require special chemical analysis, a laboratory environment, nor does it require a variety of complicated apparatus; the process does not require assessment of a variety of diverse factors or measurements; and the results may be obtained very quickly and will be accurate.

The foregoing disclosure and description of the invention are illustrative and explanatory thereof, and various changes in the size, shape, and materials may be made without departing from the spirit of the invention. For example, if greater accuracy is required as to the gas presence and volume in the sample of the evaporite formation, the sound recordings can be digitized for computer analysis.

What is claimed is:

1. A method of determining the presence and magnitude of gas content in geological formations prior to mining and release of a gas into a mine environment, comprising the steps of:
    (a) obtaining a small grab sample from the formation to be mined within a mine complex:
    (b) placing said sample into a container of solvent liquid;
    (c) placing said container, liquid and sample contained therein within a soundproof chamber;
    (d) sensing the level of acoustic emissions from said sample as it dissolves in said liquid; and
    (e) monitoring the level of acoustic emissions and based thereon determining the relative volume of gas of the sample compared to previous other samples tested.

2. The method of claim 1 wherein the sample is comprised of a relatively impermeable evaporite formation.

3. The method of claim 2 wherein the level of acoustic emissions is recorded for a time period of predetermined duration.

4. The method of claim 3 wherein the acoustic emissions produced by dissolving an evaporite sample in the liquid are recorded on a strip-chart recorder to produce a graphic representation of the decibel level of acoustic emissions per unit of time.

5. A method for determining the presence and magnitude of the gas content of an evaporite formation comprising the steps of:
    (a) obtaining a small sample from the formation to be mined;
    (b) placing said sample into a container of water, which container with sample and water is then placed into a sound-proof chamber;
    (c) sensing the acoustic emissions from said sample as it dissolves in the water;
    (d) recording the level of acoustic emissions produced as the sample dissolves during a time period of predetermined duration; and
    (e) predicting the volume of gas contained in the evaporite formation to be mined.

* * * * *